(12) United States Patent
Connor

(10) Patent No.: US 6,320,080 B2
(45) Date of Patent: *Nov. 20, 2001

(54) BRANCHED SURFACTANT MANUFACTURE

(75) Inventor: Daniel Stedman Connor, Cincinnati, OH (US)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/170,694

(22) Filed: Oct. 13, 1998

Related U.S. Application Data

(63) Continuation of application No. PCT/US97/06485, filed on Apr. 16, 1997.
(60) Provisional application No. 60/015,521, filed on Apr. 16, 1996.

(51) Int. Cl.$^7$ .......................... C07K 315/00; C07K 27/08
(52) U.S. Cl. .............................. 568/28; 568/898
(58) Field of Search ...................... 568/28, 898; 510/536

(56) References Cited

U.S. PATENT DOCUMENTS

| | | | |
|---|---|---|---|
| 2,695,327 | 11/1954 | Ziegler et al. | 260/683.15 |
| 3,480,556 | 11/1969 | DeWitt et al. | 252/152 |
| 3,647,906 | 3/1972 | Farley | 260/683 |
| 3,887,624 | 6/1975 | Gibson et al. | 260/615 B |
| 3,922,332 | 11/1975 | Schenk | 423/268 |
| 4,102,823 | 7/1978 | Matheson | 252/533 |
| 4,732,707 | 3/1988 | Naik et al. | 252/548 |
| 4,870,038 | 9/1989 | Page et al. | 502/62 |
| 5,026,933 | 6/1991 | Blain et al. | 585/7 |
| 5,245,072 | 9/1993 | Giacobbe et al. | 560/99 |
| 5,284,989 | 2/1994 | Apelian et al. | 585/533 |
| 5,446,213 | 8/1995 | Sato et al. | 568/883 |
| 5,562,866 | 10/1996 | Hu et al. | 510/432 |
| 5,780,694 | 7/1998 | Singleton | 568/909 |

FOREIGN PATENT DOCUMENTS

| | | | |
|---|---|---|---|
| 2243307 | 9/1972 | (DE) . | |
| 0342917 | 11/1989 | (EP) . | |
| 0401642 | 12/1990 | (EP) . | |
| 0439316 | 7/1991 | (EP) . | |
| 0684300 | 11/1995 | (EP) . | |
| 1151630 | 2/1958 | (FR) . | |
| 2176794 | 11/1973 | (FR) . | |
| 2267369 | 7/1975 | (FR) . | |
| 2424316 | 11/1979 | (FR) . | |
| 719445 | 12/1954 | (GB) . | |
| 1399966 | 7/1975 | (GB) . | |
| 102099 | of 1973 | (JP) . | |
| 46-2666 | 1/1971 | (JP) | C08F/26/141 |
| 49-2962 | 1/1974 | (JP) | C11D/1/14 |
| 7-62387 | 3/1995 | (JP) | C11D/1/72 |
| WO 85/02175 | 5/1985 | (WO) . | |
| WO 94/11488 | 5/1994 | (WO) . | |
| WO 96/18711 | 6/1996 | (WO) . | |
| WO 97/01521 | 1/1997 | (WO) . | |
| WO 97/38956 | 10/1997 | (WO) . | |
| WO 97/38957 | 10/1997 | (WO) . | |
| WO 97/38972 | 10/1997 | (WO) . | |
| WO 97/39087 | 10/1997 | (WO) . | |
| WO 97/39088 | 10/1997 | (WO) . | |
| WO 97/39089 | 10/1997 | (WO) . | |
| WO 97/39090 | 10/1997 | (WO) . | |
| WO 97/39091 | 10/1997 | (WO) . | |
| WO 98/23566 | 6/1998 | (WO) . | |
| WO 98/23712 | 6/1998 | (WO) . | |
| WO 98/35553 | 8/1998 | (WO) . | |

OTHER PUBLICATIONS

R. G. Laughlin, "The Aqueous Phase Behavior of Surfactants", *Academic Press*, N.Y. (1980), p. 347.

Finger, et al., "Detergent Alchohols—the effect of alcohol structure and molecular weight on surfactant properties", *J. Amer. Oil Chemists' Society*, vol. 44, (1967), p. 525.

Technical Bulletin, Shell Chemical Company, SC:364–80, 1990.

K. R. Wormuth, et al., "Phase Behavior of Branched Surfactants in Oil and Water", *Langmuir*, vol. 7, (1991), pp. 2048–2053.

R. Varadaraj, et al., "Fundamental Interfacial Properties of Alkyl–Branched Sulfate and Ethoxy Sulfate Surfactants Derived from Guerbet Alcohols. 1. Surface and Instantaneous Interfacial Tensions", *J. Phys. Chem.*, vol. 95 (1991), pp. 1671–1676.

R. Varadaraj, et al., "Relationship between Fundamental Interfacial Properties and Foaming in Linear and Branched Sulfate, Ethoxysulfate, and Ethoxylate Surfactants", *Journal of Colloid and Interface Science*, vol. 140, No. 1 (Nov. 1990), pp. 31–34.

R. Varadaraj, et al., "Micropolarity and Water Penetration in Micellar Aggregates of Linear and Branched Hydrocarbon Surfactants", *Langmuir*, vol. 6 (1990), pp. 1376–1378.

R. Varadaraj, et al., "Relationship between Dynamic Contract Angle and Dynamic Surface Tension Properties for Linear and Branched Ethoxylate, Ethoxysulfate, and Sulfate Surfactants", *Journal of Colloid and Interface Science*, vol. 147, No. 2 (Dec. 1991), pp. 403–406.

R. D. Swisher, "Surfactant Biodegradation", *Surfactant Science Series*, 2$^{nd}$ Ed., Marcel Dekker, Inc., vol. 18, pp. 20–29 and 34–36, 1992.

CEH Marketing Research Report "Detergent Alcohols", by R. F. Modler, et al., *Chemical Economics Handbook*, (1993), pp. 609.5000–609.5002.

"Alcohols, Higher Aliphatic", *Kirk Othmer's Encyclopedia of Chemical Technology*, 4$^{th}$ Ed., Wiley, N.Y., (1991), vol. 1, pp. 865–913.

"Liquid Fuels", *Kirk Othmer's Encyclopedia of Chemical Technology*, Wiley, N.Y., (1989), vol. 11, pp. 447–489.

"Oxo Process", *Kirk Othmer's Encyclopedia of Chemical Technology*, Wiley, N.Y., (1989), vol. 16, pp. 634–653.

"Sasol Detergent Alcohols", R&D Technical Bulletin, Sasol Alpha Olefins, (Oct. 1, 1996), pp. 1–12.

*Primary Examiner*—Joseph K. McKane
*Assistant Examiner*—Joseph Murray
(74) *Attorney, Agent, or Firm*—Joseph Taffy; C. Bryant Cook; Kim W. Zerby

(57) ABSTRACT

Alpha-olefins are dimerized to form branched-chain feedstocks for detersive surfactants.

2 Claims, No Drawings

BRANCHED SURFACTANT MANUFACTURE

CROSS REFERENCE

This is a continuation of PCT International application Serial No. PCT/US97/06485, filed Apr. 16, 1997; which claim priority to Provisional Application Ser. No. 60/015,521, filed Apr. 16, 1996.

FIELD OF THE INVENTION

The present invention relates to processes for manufacturing detersive surfactants, especially those containing branched-chain hydrophobic units.

BACKGROUND OF THE INVENTION

Conventional detersive surfactants comprise molecules having a water-solubilizing substituent (hydrophilic group) and an oleophilic substituent (hydrophobic group). Such surfactants typically comprise hydrophilic groups such as carboxylate, sulfate, sulfonate, amine oxide, polyoxyethylene, and the like, attached to an alkyl, alkenyl or alkaryl hydrophobe usually containing from about 10 to about 20 carbon atoms. Accordingly, the manufacturer of such surfactants must have access to a source of hydrophobe groups to which the desired hydrophile can be attached by chemical means. The earliest source of hydrophobe groups comprised the natural fats and oils, which were converted into soaps (i.e., carboxylate hydrophile) by saponification with base. Coconut oil and palm oil are still used to manufacture soap, as well as to manufacture the alkyl sulfate ("AS") class of surfactants. Other hydrophobes are available from petrochemicals, including alkylated benzene which is used to manufacture alkyl benzene sulfonate surfactants ("LAS").

The literature asserts that certain branched hydrophobes can be used to advantage in the manufacture of alkyl sulfate detersive surfactants; see, for example, U.S. Pat. No. 3,480,556 to deWitt, et al., Nov. 25, 1969. However, it has been determined that the beta-branched surfactants described in the '556 patent are inferior with respect to certain solubility parameters, as evidenced by their Krafft temperatures. It has further been determined that surfactants having branching towards the center of carbon chain of the hydrophobe have much lower Krafft temperatures. See: "The Aqueous Phase Behavior of Surfactants", R. G. Laughlin, Academic Press, New York (1994) p. 347. Accordingly, it has now been determined that such surfactants are preferred for use especially under cool or cold water washing conditions (e.g., 20° C.–5° C.).

One problem associated with the manufacture of detersive surfactants having hydrophobe groups with mid- or near-mid chain branching is the lack of a ready source of such hydrophobes. By the present invention, a process is described for manufacturing such branched hydrophobes and converting them into mid- or near-mid chain branched surfactants.

SUMMARY OF THE INVENTION

The present invention encompasses a process for preparing mid- to near mid-chain branched olefins (primarily, methyl branched at or near the mid-chain region). Such materials are then used as the basic feedstock which provides the hydrophobic portion of branched-chain detersive surfactants.

The process herein is illustrated by the following reaction sequence.

1) Alpha-Olefin Dimerization

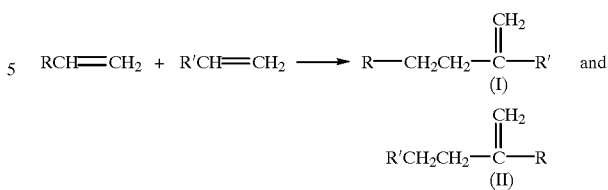

wherein R and R' may be the same or different linear alkyl, and wherein R is $C_3$–$C_7$, preferably $C_5$ to $C_7$ linear alkyl, and R' is $C_3$–$C_7$, preferably $C_5$–$C_7$ linear alkyl. For use in preparing surfactants in cleaning products such as laundry detergents, dishwashing liquids, and the like, R and R' are preferably the same or within one or two carbon atoms of each other in chain length. Some linear olefins may also result from the dimerization and these can optionally be removed using molecular sieves. Step 1 of the process herein is designed to provide branched olefins which preferably contain from about 12 to about 18 (avg.) total carbon atoms.

2) Alcohol Production

In Step 2 (Route A), the olefin mixture for Step 1 can be pre-randomized to enhance the ultimate formation of alcohols (i) and (ii) in subsequent Step 3. Alternatively (Step 2, Route B), this pre-randomization step can be deleted and the Oxo catalyst, itself, can randomize the final product among the three possible terminal positions.

Route A

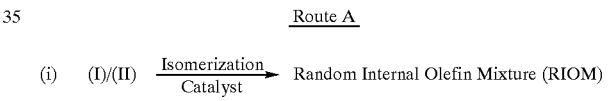

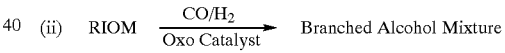

Route B

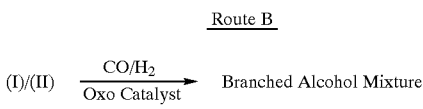

The Oxo process to make alcohols is described in detail in Kirk-Othmer *Encyclopedia of Chemical Technology*, 4th Edition, Volume 1, pp. 903–8 (1991), Jacqueline I. Kroschwitz, Executive Editor, Wiley-Interscience, New York. The catalyst for this step is, for example, cobalt-carbon monoxide-organophosphine.

The alcohol mixture of Step (2) of the present process comprises branched-chain primary alcohol compounds of the following formulae for use in Step (3), below.

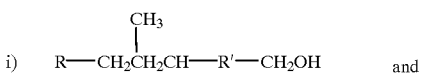

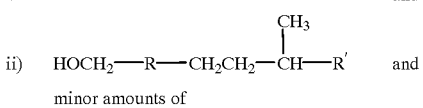

minor amounts of

-continued

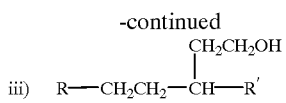

It is to be understood that when CH$_2$OH is substituted on R or R' it is primarily on their respective terminal carbons or to a lesser extent on their penultimate carbons. Desirably, minimal amounts of compounds of the formula (iii) are present in Step (3).

3) Surfactant Production

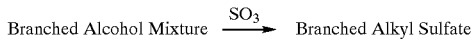

Advantageously, the present process results in no geminal branching, i.e., no "quaternary" carbon substitution. Steric hindrance will block inverse addition to vinylidene carbon with cobalt-carbon monoxide-organophosphine which otherwise would form a non-biodegradable quaternary carbon. Moreover, little (less than about 3%) vicinal branching occurs. Of course, some of the overall feedstock may remain unbranched. Typically, and preferably from the standpoint of cleaning performance and biodegradability, the present process provides hydrophobes with one near-central methyl in the case of isomers i) and ii).

All percentages, ratios and proportions herein are by weight, unless otherwise specified. All documents cited herein are, in relevant part, incorporated herein by reference.

DETAILED DESCRIPTION OF THE INVENTION

1) Olefin Dimerization

The present invention encompasses, in a process for preparing surfactant precursor hydrophobes from dimerization of two same or near same chain length alpha-olefins to form a detergent range vinylidene olefin. These alpha olefins $C_5$ to $C_{10}$, preferably $C_7$ to $C_9$ are dimerized to give $C_{10}$ to $C_{20}$, preferably $C_{14}$ to $C_{18}$ vinylidene olefins which upon Oxo reaction give $C_{11}$ to $C_{21}$, preferably $C_{15}$ to $C_{19}$ alcohols. There are a number of processes for accomplishing said dimerization; see U.S. application Ser. No. 9,200,398, U.S. Pat. Nos. 4,658,078, 4,973,788; O. S. Vostrikova, A. G. Ibragimov, G. A. Tolstikov, L. M. Zelenova and U. M. Dzhemilev, Izv. Akad. Nauk SSSR, Ser. Khim. (1980), (10), 2330–2 [Chem. Abstr. 94:65032]; Jpn. Kokai Tokkyo Koho, 06228016 A2 [Chem. Abstr. 122:186930].

2) Alcohol Production

Route A

Part a)

The carbon-carbon double bond of the vinylidene olefin is pre-isomerized using a method such as Shell uses to isomerize alpha-olefins in their SHOP process; see *Kirk-Othmer Encyclopedia of Chemical Technology*, 4th Edition, Volume 17, pp. 848–50 (1996), Jacqueline I. Kroschwitz, Executive Editor, Wiley-Interscience, New York and Chemical Economics Handbook, pp. 681.5030K-L, Stanford Research Institute, Menlo Park, Calif. 94025, October 1993.

Part b)

Oxo chemistry is used to convert the pre-isomerized vinylidene olefin (now largely internal olefin) to a primary alcohol mixture. For this an Oxo catalyst which isomerizes the double bond to alpha positions prior to carbonylation is desired as is the case using cobalt-carbonyl-phosphine catalysts in the one step process, see *Kirk-Othmer Encyclopedia of Chemical Technology*, 4th Edition, Volume 1, pp. 903–8 (1991). Route A, (that is including pre-isomerization) is undertaken to assure relatively high yields of alcohols i and ii versus alcohol iii. Note alcohol sulfates of i and ii are desired surfactants whereas that of iii may be deficient.

Route B

This step utilizes the same Oxo catalyst on the vinylidene olefin directly without its pre-isomerization. This relies upon the catalyst to completely isomerize the carbon-carbon double bond of the vinylidene olefin prior to carbonylation. The object is to obtain as much i and ii relative to iii as is obtained in Route A.

Other fatty alcohol-derived surfactants can also be made, e.g., alkyl ethoxyl sulfates (AES), alkyl polyglucosides (APG), etc. Note that surfactants other than alcohol sulfates or AES may be made by oxidizing said alcohol or its aldehyde intermediate into a carboxylate (i.e., a branched-chain soap). This soap can be an excellent surfactant and/or detergent builder in and of itself. This carboxylate can also be used as a feedstock and converted to branched acyl-taurates, -isethionates, -sarcosinates, -N-methylglucamide or other acyl-derived surfactants using art-disclosed techniques.

INDUSTRIAL APPLICABILITY

Branched-chain surfactants of the type resulting from the present process can be used in all manner of cleaning compositions. Such compositions include, but are not limited to: granular, bar-form and liquid laundry detergents; liquid hand dishwashing compositions; liquid, gel and bar-form personal cleansing products; shampoos; dentifrices; hard surface cleaners, and the like. Such compositions can contain a variety of conventional detersive ingredients. The following listing of such ingredients is for the convenience of the formulator, and not by way of limitation of the types of ingredients which can be used with the branched-chain surfactants herein.

The branched-chain surfactants herein can be used in combination with detergency builders. Such builders include, for example, 1–10 micrometer zeolite A, polycarboxylate builders such as citrate, layered silicate builders such as "SKS-6" (Hoechst) and phosphate materials, especially sodium tripolyphosphate ("STPP"). Most laundry detergents typically comprise at least about 1% builder, more typically from about 5% to about 80% builder or mixtures of builders.

Enzymes, such as proteases, amylases, lipases, cellulases, peroxidases, and mixtures thereof, can be employed in detergent compositions containing the branched-chain surfactants. Typical detergent compositions comprise from about 0.001% to about 5% of commercial enzymes.

Detergent compositions can also contain polymeric soil release agents (SRA's). Such materials include, for example, anionic, cationic and non-charged monomer units, especially polyester materials. Preferred materials of this type include oligomeric terephthalate esters, sulfonated substantially linear ester oligomers comprising a backbone of terephthaloyl and oxyalkyleneoxy repeat units and phthalolyl-derived sulfonated terminal moieties. A variety of SRA's are described, for example, in U.S. Pat. Nos. 4,968,451; 4,711,730; 4,721,580; 4,702,857; 4,877,896; 5,415,807; and in other literature references. Such soil release materials typically comprise from about 0.01% to about 10% of finished detergent compositions.

Detergent compositions may also optionally contain bleaching compositions comprising a bleaching agent and one or more bleach activators. If present, bleaching agents such as percarbonate or perborate (especially perborate monohydrate "PB1") typically are used at levels from about 1% to about 30% of finished detergent compositions. Bleach activators such as nonanoyloxy-benzene sulfonate ("NOBS") and tetraacetyl ethylenediamine ("TAED"), and mixtures thereof, can be used to enhance the bleaching activity of materials such as perborate and percarbonate. If present, the amount of bleach activator will typically be from about 0.1% to about 60% of a bleaching composition comprising a bleaching agent-plus-bleach activator. Other bleaching agents such as the so-called "photoactivated" bleaches (see U.S. Pat. No. 4,033,718) can also be used. Sulfonated zinc phthalocyanine is an especially preferred photoactivated bleaching agent.

Detergent compositions can also contain clay soil removal/antiredeposition agents such as ethoxylated tetra-ethylene pentamine; see U.S. Pat. No. 4,597,898. Such materials typically comprise from about 0.01 to about 10% to about 1001% of fully-formulated laundry detergents.

Detergent compositions can also contain from about 0.1% to about 7% of polymeric dispersing agents, which are especially useful in the presence of zeolite and/or layered silicate builders. Such materials are known in the art (see U.S. Pat. No. 3,308,067). Such materials include acrylate/malic-based copolymers, such as described in EP 193,360, as well as polyethylene glycol ("PEG").

Detergent compositions herein can also include various brighteners, dye transfer inhibiting agents (especially polymers of N-vinylpyrrolidone and N-vinylimidazole), suds suppressors (especially silicones), chelating agents such as nitilotiacetate, ethylenediamine disuccinate, and the like. Such materials will typically comprise from about 0.5% to about 10%, by weight, of fully-formulated cleaning compositions.

Moreover, it is to be understood that the branched-chain surfactants prepared in the manner of the present invention may be used singly in cleaning compositions or in combination with other detersive surfactants. Typically, fully-formulated cleaning compositions will contain a mixture of surfactant types in order to obtain broadscale cleaning performance over a variety of soils and stains and under a variety of usage conditions. One advantage of the branched-chain surfactants herein is their ability to be readily formulated in combination with other known surfactant types. Nonlimiting examples of additional surfactants which may be used herein typically at levels from about 1% to about 55%, by weight, include the unsaturated sulfates such as oleyl sulfate, the $C_{10}$–$C_{18}$ allyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10\text{-}18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. Nonionic surfactants such as the ethoxylated $C_{10}$–$C_{18}$ alcohols and alkyl phenols, (e.g., $C_{10}$–$C_{18}$ EO (1–10) can also be used. If desired, other conventional surfactants such as the $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. $C_{10}C_{14}$ alkyl benzene sulfonates (LAS), which are often used in laundry detergent compositions, can also be used with the branched surfactants herein.

The following Examples illustrate the use of branched-chain surfactants prepared according to the present invention in various cleaning compositions, but is not intended to be limiting thereof.

EXAMPLE I

Granular laundry detergents are prepared as follows.

|  | A | B | C |
|---|---|---|---|
| Blown Powder |  |  |  |
| Zeolite A | 30.0 | 22.0 | 6.0 |
| Sodium sulfate | 19.0 | 5.0 | 7.0 |
| Polyacrylate |  |  |  |
| LAS | 13.0 | 11.0 | 21.0 |
| Branched AS* | 9.0 | 8.0 | 8.0 |
| Silicate, Na | — | 1.0 | 5.0 |
| Soap | — | — | 2.0 |
| Carbonate, Na | 8.0 | 16.0 | 20.0 |
| Spray On |  |  |  |
| $C_{14\text{–}15}EO7$ | 1.0 | 1.0 | 1.0 |
| Dry additives |  |  |  |
| Protease | 1.0 | 1.0 | 1.0 |
| Lipase | 0.4 | 0.4 | 0.4 |
| Amylase | 0.1 | 0.1 | 0.1 |
| Cellulase | 0.1 | 0.1 | 0.1 |
| NOBS | — | 6.1 | 4.5 |
| PB1 | 1.0 | 5.0 | 6.0 |
| Sodium sulfate | — | 6.0 | — |
| Moisture & Miscellaneous | --------------Balance------------- | | |

*$C_{12}$—$C_{14}$ methyl branched alkyl sulfate, prepared as disclosed above.

A bleach-containing nonaqueous liquid laundry detergent is prepared as follows.

EXAMPLE II

| Component | Wt. % | Range (% wt.) |
|---|---|---|
| Liquid Phase |  |  |
| Branched AS* | 25.3 | 18–35 |
| $C_{12\text{–}14}$, EO5 alcohol ethoxylate | 13.6 | 10–20 |
| Hexylene glycol | 27.3 | 20–30 |
| Perfume | 0.4 | 0–1.0 |
| Solids |  |  |
| Protease enzyme | 0.4 | 0–1.0 |
| $Na_3$ Citrate, anhydrous | 4.3 | 3–6 |
| Sodium perborate (PB-1) | 3.4 | 2–7 |
| Sodium nonanoyloxybenzene sulfonate (NOBS) | 8.0 | 2–12 |
| Sodium carbonate | 13.9 | 5–20 |
| Diethyl triamine pentaacetic acid (DTPA) | 0.9 | 0–1.5 |
| Brightener | 0.4 | 0–0.6 |
| Suds Suppressor | 0.1 | 0–0.3 |
| Minors | -----Balance----- | |

*$C_{12}$—$C_{16}$ methyl branched alkyl sulfate, Na salt, prepared as disclosed above.

A hand dishwashing liquid is as follows.

| Ingredient | % (wt.) | Range (% wt.) |
|---|---|---|
| Branched AS* | 13.0 | 5–15 |
| Ammonium $C_{12-13}$ alkyl ethoxy sulfate | 15.0 | 10–35 |
| Coconut amine oxide | 2.6 | 2–5 |
| Betaine**/Tetronic 704 ® | 0.87–0.10 | 0–2 (mix) |
| Alcohol Ethoxylate $C_8E_{11}$ | 5.0 | 2–10 |
| Ammonium xylene sulfonate | 4.0 | 1–6 |
| Ethanol | 4.0 | 0–7 |
| Ammonium citrate | 0.06 | 0–1.0 |
| Magnesium chloride | 3.3 | 0–4.0 |
| Calcium chloride | 2.5 | 0–4.0 |
| Ammonium sulfate | 0.08 | 0–4.0 |
| Hydrogen peroxide | 200 ppm | 0–300 ppm |
| Perfume | 0.18 | 0–0.5 |
| Maxatase ® protease | 0.50 | 0–1.0 |
| Water and minors | --------------Balance---------- | |

*$C_{12}C_{14}$ methyl branched alkyl sulfate, triethanolammonium salt, prepared as disclosed above.
**Cocoalkyl betaine.

What is claimed is:

1. A process for preparing branched alkyl carboxylate surfactants, comprising the steps of:

(a) dimerizing alpha olefins of the formula $RCH=CH_2$ and $R'CH_2=CH_2$, to form olefins of the formula:

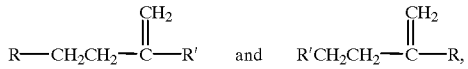

wherein in the above formulas R and R' may be the same or different $C_3$ to $C_7$ linear alkyl substituents; followed by either (b) isomerizing the olefins from Step (a) and the subsequent reaction of said isomerized olefins with $CO/H_2$ under Oxo conditions using a cobalt-carbonyl-phosphine catalyst; or directly reacting the olefins from Step (a) with $CO/H_2$ under Oxo conditions using a cobalt-carbonyl-phosphine catalyst; and (c) recovering branched alcohols of the formula:

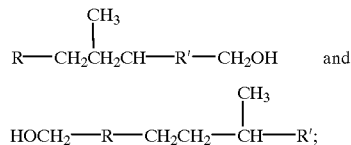

(d) oxidizing the alcohols or their aldehyde intermediates recovered from Step (c); and, (e) recovering the desired branched alkyl carboxylate surfactants.

2. A process for preparing branched acyl taurate, branched acyl isethionates, branched acyl sarcosinates, or branched acyl N-methylglucamine surfactants using the branched alkyl carboxylate surfactants prepared according to claim 1 as a feedstock.

* * * * *

UNITED STATES PATENT AND TRADEMARK OFFICE
CERTIFICATE OF CORRECTION

PATENT NO.    : 6,320,080 B2  
DATED         : November 20, 2001  
INVENTOR(S)   : Daniel S. Connor Page 1 of 1

It is certified that error appears in the above-identified patent and that said Letters Patent is hereby corrected as shown below:

<u>Column 2,</u>  
Line 60, replace

"R—CH$_2$CH$_2$CH(CH$_3$)—R'—CH$_2$OH"   with

--R—CH$_2$CH(CH$_3$)CH$_2$—R'—CH$_2$OH--

<u>Column 7,</u>  
Line 27, replace "R'CH$_2$=CH$_2$" with --R'CH=CH$_2$--;

<u>Column 8,</u>  
Line 15, replace

"R—CH$_2$CH$_2$CH(CH$_3$)—R'—CH$_2$OH"   with

--R—CH$_2$CH(CH$_3$)CH$_2$—R'-CH$_2$OH--

Signed and Sealed this

Nineteenth Day of November, 2002

*Attest:*

JAMES E. ROGAN  
*Attesting Officer*     *Director of the United States Patent and Trademark Office*